United States Patent [19]

Armenta et al.

[11] Patent Number: 4,775,626

[45] Date of Patent: Oct. 4, 1988

[54] METHOD AND COMPOSITIONS FOR PROTECTING ANEROBIC MICROORGANISMS

[75] Inventors: Richard Armenta, Sunnyvale; Ian Gibbons, Menlo Park; Edwin F. Ullman, Atherton, all of Calif.

[73] Assignee: Syntex (U.S.A.) Inc., Palo Alto, Calif.

[21] Appl. No.: 866,824

[22] Filed: May 23, 1986

[51] Int. Cl.$^4$ .................................................. C12N 1/38
[52] U.S. Cl. ................................... 435/244; 435/253; 435/254; 435/801; 435/818; 435/189
[58] Field of Search ................ 435/801, 818, 189, 244

[56] References Cited

U.S. PATENT DOCUMENTS 3,939,044  2/1976  Wilkins et al. .
4,476,224  10/1984  Adler ................................. 435/801

OTHER PUBLICATIONS

Crow et al.-J. Microbiol. Methods, vol. 4, (1985), pp. 133–139.

*Primary Examiner*—Sam Rosen
*Attorney, Agent, or Firm*—Theodore J. Leitereg

[57] ABSTRACT

A method is disclosed for reducing the oxygen content of a medium in which are present cells, usually anaerobic microorganisms, to extend the time during which the cells remain viable. The method comprises having in fluid contact with the aqueous medium an effective amount of an oxidase and substrate for the oxidase. The oxidase and substrate for the oxidase in an aqueous medium can be in fluid, e.g., air, contact with a separately contained aqueous medium in which the cells are present. Alternatively, the cells can be present in the same aqueous medium as the oxidase and substrate for the oxidase. The aqueous medium containing the oxidase and the substrate for the oxidase can further contain a hydrogen peroxide scavenger in an effective amount. A composition in accordance with the invention comprises in a liquid medium viable cells, such as anaerobic microorganisms, an oxidase and its substrate in an amount sufficient to retain the viability of the cells, and a hydrogen peroxide scavenger in an amount sufficient to reduce the level of hydrogen peroxide generated by the oxidase. The method of the invention has particular application in transport media used for transporting microbiological specimens.

29 Claims, 1 Drawing Sheet

METHOD AND COMPOSITIONS FOR PROTECTING ANEROBIC MICROORGANISMS

BACKGROUND OF THE INVENTION

1. Field of the Invention

This invention relates to the protection of cells, usually anaerobic microorganisms. There are a number of situations where the retention of viability of anaerobic microorganisms is important. One such situation is in diagnostic assays for determining the presence of a pathogenic microorganism. In such assays it is important that the anaerobic microorganism remain viable between the period beginning with the collection of a specimen from a patient and ending with the diagnostic assay being conducted on the specimen. Loss of viability of the microorganism will result in a false test with obvious consequences.

The transport and culture of anaerobic microorganisms requires the use of a system that prevents the microorganism from being killed by exposure to oxygen. In one approach air containing oxygen is substituted by oxygen-free nitrogen or carbon dioxide, Special media are conventionally employed. Other approaches employ media containing ingredients such as sodium thioglycollate, cysteine, sodium sulfide, sodium dithionite, ascorbic acid and the like that chemically combine with dissolved oxygen to deplete the oxygen content of the culture medium. For routine procedures for maintaining anaerobic microorganisms, microbiologists use reducing media stored in ordinary tightly capped test tubes. Other systems employed to reduce oxygen in working with cultures of anaerobic microorganisms, particularly with petri plates, involve packets of chemicals, e.g., sodium bicarbonate, sodium borohydride, and palladium, contained in a sealed container. The palladium serves as a catalyst to cause the oxygen to react with hydrogen produced by hydrolysis of the borohydride to produce water.

2. Description of the Related Art

Oxygen and the metabolism of *Peptostreptococcus anaerobius* UPI 4330-1 is discussed by Hoshino, et al., *Journal of General Microbiology* (1978) 107:235-248. Oxygen and the growth and metabolism of *Clostridium acetobutylicum* is disclosed by O'Brien, et al. *Journal of General Microbiology* (1971) 68: 307-318. Oxygen scavenging with enzymes is described in U.S. Pat. No. 4,414,334. The bactericidal effect of cysteine exposed to atmospheric oxygen is described by Carlsson, et al., *Applied and Environmental Microbiology* (1979) 37: 383-390. Immobilized glucose oxidase and its use for oxygen removal from beer is described by Hartmeier et al., *MBAA Technical Quarterly* (1981) 18: 145-149. Basic trials or possible industrial applications of an immobilized glucose oxidase-catalase system is disclosed by Hartmeier in *Biotechnol. Lett.* (1979) 1:21-26. Deoxygenation of protective coating compositions, e.g., paints, the compositions, and their use are disclosed in Eur. Pat. Appl. EP55240A1. The possibility that endogenous catalase and/or peroxidase protects certain anaerobes against oxygen is discussed by Morris, *J. Appl. Bacteriol.* (1976) 40:229-244.

SUMMARY OF THE INVENTION

The present invention is directed to methods and compositions for reducing the toxic effects of oxygen on cells, usually anaerobic microorganisms. The method comprises having present with the cells an effective amount of an oxidase and substrate for the oxidase. The cells can be present in an aqueous medium and the medium may itself contain an oxidase and its substrate. Alternatively, the oxidase and its substrate can be contained independent of the cells where both are in fluid contact with one another. Since hydrogen peroxide is generated by the oxidase-substrate reaction, a scavenger can also be included to destroy the hydrogen peroxide, for example by disproportionation of hydrogen peroxide to oxygen and water.

The present invention also includes a composition comprising viable cells such as anaerobic microorganisms, an oxidase and its substrate in an amount sufficient to reduce the toxic effect of oxygen on the cells, and a hydrogen peroxide scavenger in an amount sufficient to reduce the level of hydrogen peroxide generated by the oxidase. The invention further includes kits comprising novel reagents of the present invention in packaged combination for use in accordance with the present invention.

DESCRIPTION OF THE SPECIFIC EMBODIMENTS

Figure 1:
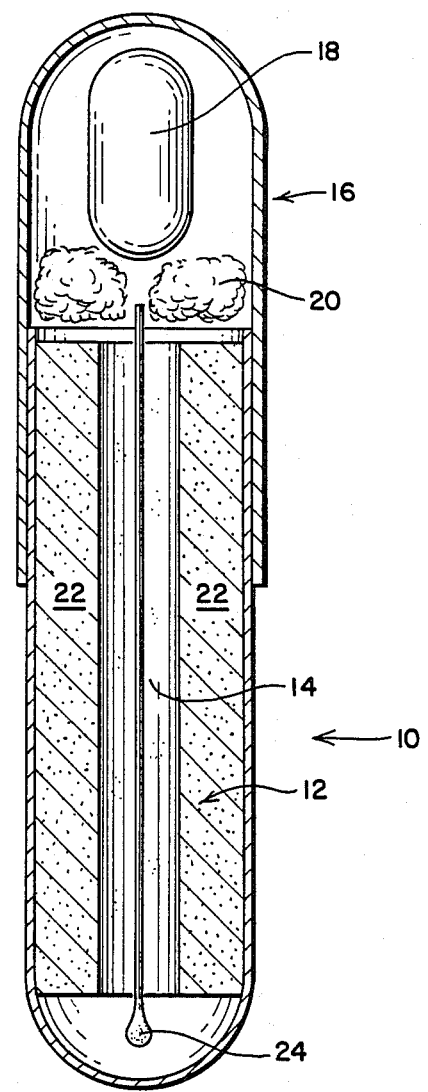

The present invention concerns the protection of cells, particularly anaerobic microorganisms, against the toxic effects of oxygen wherein an agent is employed for such protection. The improvement of the present invention comprises employing as such an agent an oxidase and its corresponding substrate in an amount effective to reduce the oxygen concentration sufficiently to protect the cells from the effect of oxygen toxicity. One aspect of the invention relates to a method for reducing the oxygen content of a fluid medium in which cells are present. The method comprises having in contact with the fluid medium an effective amount of an oxidase and substrate for the oxidase. The method can further comprise the use of an effective amount of a hydrogen peroxide scavenger to reduce the level of hydrogen peroxide generated during the reaction of the oxidase with its substrate.

Before proceeding further with a description of the present invention, a number of terms will be defined.

"Cell" means a unicellular organism such as a bacterium, and also refers to normal and transformed cells, usually mammalian, obtained from biopsy, scraping, exudates, sputum, blood, lymphaticfluid, cerebral spinal find and the like, either infected or not infected, cultured or not cultured.

"Anaerobic microorganism" means a microorganism that is sensitive to oxygen. The sensitivity to oxygen can be exhibited as a lethal effect on the microorganism, or by modification of the growth characteristics or by inhibition of growth of the microorganism. Microorganisms differ in their sensitivity to oxygen such that a continuous spectrum of oxygen tolerance from the most sensitive, strict anaerobe to the least sensitive hyper aerobe is observed. Tolerance of air at one atmosphere containing approximately twenty percent oxygen represents but one line drawn on this spectrum of oxygen sensitivity, which extends below, as well as above, this particular concentration of oxygen. When the anaerobic microorganism is present in an aqueous medium, the dissolved oxygen concentration or the dissolved oxygen tension can be referred to in viewing this spectrum of oxygen sensitivity. For strict anaerobic microorganisms even very low concentrations (less than 10 $\mu$M) of dissolved oxygen tension are inhibitory to growth. Facultative anaerobes are distinguished by being able to grow either with or without oxygen. The term "microaerophilic" may be applied to aerobes or facultative anaerobes for which the inhibitory dissolved oxygen tension is less than 0.2 atmospheres, which is the oxygen partial pressure in air at one atmosphere. For other aerobic microorganisms the inhibitory dissolved oxygen tension is hyperbaric, that is, greater than 0.2 atmospheres. Thus, the inhibitory dissolved oxygen tension for aerobes may be sufficiently low to permit large scale fermentation in air. For purposes of the present invention, the term anaerobic microorganism will apply to all microorganisms that exhibit sensitivity to oxygen at or below its normal atmospheric partial pressure. The present invention has application to most situations where it is desirable to reduce the effects of oxygen on cells, particularly anaerobic microorganisms.

Exemplary of anaerobic microorganisms are bacteria, particularly, Treponema spp., such as *T. denticola;* Selenomonas spp., such as *S. ruminatum;* Clostridium spp., such as *C. perfringens;* Bacteroides spp., such as *B. fragilis;* Peptostreptococcus spp., such as *P. anaerobius;* Eubacterium spp., such as *E. lentum;* Peptococus spp., such as *Pc. assaccharolyticus;* Veillonella spp., such as *V. parvula,* Propionibacterium spp., such as *Pr. acnes;* Actinomyces spp., such as *A. israelii,* and Fusobacterium spp, such as *F. necrophorum.*

"Oxidase" includes those enzymes in the classification oxidoreductase with oxygen as acceptor, classification 1.1.3. A preferred group of oxidase enzymes for purposes of the invention are mono- and polyol oxidases, particularly sugar oxidases. Exemplary of oxidase enzymes that can be employed in the present invention are glucose oxidase, hexose oxidase, galactose oxidase, pyranose oxidase, sorbose oxidase, glycollate oxidase, malate oxidase, cholesterol oxidase, arylalcohol oxidase, alcohol oxidase, gluconolactone oxidase, pyridoxine oxidase, catechol oxidase, choline oxidase, and the like.

Exemplary oxidase enzymes and their substrates and the reactions involved are summarized in the following table.

| | |
|---|---|
| Glycollate oxidase | Glycollate + $O_2$ = glyoxylate + $H_2O_2$ |
| Malate oxidase | L-Malate + $O_2$ = oxaloacetate + (?) |
| Glucose oxidase | $\beta$-D-Glucose + $O_2$ = D-glucono-$\delta$-lactone + $H_2O_2$ |
| Hexose oxidase | $\beta$-D-Glucose + $O_2$ = D-glucono-$\delta$-lactone + $H_2O_2$ |
| Cholesterol oxidase | Cholesterol + $O_2$ = 4-cholesten-3-one + (?) |
| Aryl-alcohol oxidase | An aromatic primary alcohol + $O_2$ = an aromatic aldehyde + $H_2O_2$ |
| L-Gluconolactone oxidase | L-Glucono-$\gamma$-lactone + $O_2$ = L-xylo-hexulonolactone + $H_2O_2$ |
| Galactose oxidase | D-Galactose + $O_2$ = D-galacto-hexodialdose + $H_2O_2$ |
| Pyranose oxidase | D-Glucose + $O_2$ = D-glucosone + $H_2O_2$ |
| L-Sorbose oxidase | L-Sorbose + $O_2$ = 5-keto-D-fructose + $H_2O_2$ |
| Pyridoxine 4-oxidase | Pyridoxine + $O_2$ = pyridoxal + $H_2O_2$ |
| Alcohol oxidase | Primary alcohol + $O_2$ = aldehyde + $H_2O_2$ |
| Catechol oxidase | 4 Catechol + 3 $O_2$ = |
| (dimerizing) | 2 dibenzol[1,4]dioxin-2,3-dione + 6 $H_2O_2$ |
| L-2-Hydroxyacid oxidase | L-2-Hydroxyacid + $O_2$ = 2-oxo-acid + $H_2O_2$ |
| Ecdysone oxidase | Ecdysone + $O_2$ = 3-dehydroecdysone + $H_2O_2$ |
| Choline oxidase | Choline + $O_2$ = betaine aldehyde + $H_2O_2$ |

"Hydrogen peroxide scavenger" refers to a substance which is capable of reducing the level of hydrogen peroxide generated by the reaction of the oxidase with its substrate in carrying out the method in accordance with the present invention. The hydrogen peroxide scavenger should be capable of reducing the hydrogen peroxide to water by means of a suitable reducing agent or catalyzing the disproportionation of hydrogen peroxide to oxygen and water. The hydrogen peroxide scavenger can be organic or inorganic. Organic hydrogen peroxide scavengers are enzymes, for example, catalase, peroxidase and a peroxidase substrate such as ascorbate, o-phenylenediamine, etc. and the like. Exemplary of inorganic hydrogen peroxide scavengers are sodium iodide/sodium thiosulfate, arsenite, manganese and ferrous salts, manganese dioxide, hyposulfite, sulfite and the like.

The present invention is directed to a method of reducing the oxygen content of a fluid medium in which a cell, usually an anaerobic microorganism, is present. The method comprises having in contact with the fluid medium an effective amount of an oxidase and substrate for the oxidase.

The oxidase and its substrate are usually in an aqueous medium and can be in contact with the cells by virtue of being present in an aqueous medium containing the cells. On the other hand, the contact can be achieved by having the oxidase and its substrate contained separately from the cells but in close proximity in fluid contact, preferably in a closed container. The container can be a vial, test tube, petri dish, and the like in which the cells are placed. The cells will be present in an aqueous medium. The oxidase can be present in an aqueous medium in a separate container which is placed in the container with the cells. Preferably, the container is closed by an appropriate means such as a cap, lid, or the like. Substrate for the oxidase can be present in the aqueous medium containing the oxidase initially or it can be subsequently introduced. The closed container permits the oxidase to remove oxygen from the fluid, e.g., air, in the closed container by virtue of the reaction of oxidase and its substrate.

The oxidase and its substrate are present in an effective amount, in other words, in an amount sufficient to reduce the oxygen content of the aqueous medium containing the cells to a level where toxic effects of oxygen on the cells are no longer a problem for the particular use to be applied to the cells. Cells differ in a sense by degree in their toxic reaction to oxygen. Those cells which cannot tolerate oxygen even at very low levels will therefore require higher levels of oxidase and its substrate in order to have an effective reduction of the oxygen content in the aqueous medium containing the cells. On the other hand, cells which can tolerate varying levels of oxygen would require a proportionately less amount of oxidase and its substrate in order to achieve effective reduction in the oxygen content in the aqueous medium containing those cells. The volume of the closed container and the nature of the fluid medium, i.e., gas or liquid, will also be factors for consideration in determining the amount of oxidase and its substrate. For the most part the oxidase will be present in an amount of from about 0.02 to 20 International Units per milliliter. The substrate for the oxidase will be present in an amount of from about $10^{-3}$ to 5 molar, preferably $10^{-2}$ to 1 molar. Generally, the oxidase and its substrate will be present in an aqueous medium either initially or brought together in an aqueous environment during the period of protection of the anaerobic organism. Usually the total amount of substrate will be sufficient to react with all the oxygen in the closed container, more usually, at least twice as much substrate will be employed, frequently a three to five times molar excess, over the total oxygen in the closed container.

A hydrogen peroxide scavenger, when employed, will be present in an effective amount, that is, an amount sufficient to reduce the hydrogen peroxide concentration to a level that is not toxic to the cells. In general the number of units of scavenger expressed as micromoles substrate turned over per minute will be at least equal to, more usually ten to one hundred fold or higher, the units of oxidase present in the liquid medium.

The concentration of cells present in a liquid medium, may vary widely from as few as one cell per ml to $10^9$ cells per ml, usually at least 100 cells per ml to $10^6$ cells per ml.

In carrying out the method, the oxidase and its substrate will be present, either initially or during the method, in a liquid aqueous medium. The cells will also be present in an aqueous medium, which may be the same of different than the oxidase medium. Other polar solvents compatible with the oxidase may also be employed in the oxidase medium, usually oxygenated organic solvents from one to six, more usually from one to four, carbon atoms, including alcohols, ethers, and the like. Usually these cosolvents will be present in less than about 40 weight percent, more usually in less than about 20 weight percent. The pH for the medium containing the oxidase will usually be selected to promote effective oxygen reduction and to avoid detrimental effects on the oxidase and its substrate. Generally, a pH range of 5 to 10, more usually 6 to 8, will be used. The medium containing the cells may be buffered to control pH within a range compatible with cell viability and may contain various nutrients such as amino acids, reducing agents such as thiols, e.g. cystine, and growth factors or may be an unmodified sample of tissue or body fluid. Illustrative buffers include borate, phosphate, carbonate, Tris, barbital, and the like. The particular buffer employed is not critical to this invention; however, in individual systems one buffer may be preferred over another.

Moderate temperatures are normally employed for carrying out the method and usually constant temperatures during the period for conducting the method. Generally, the temperatures will be chosen to achieve maximum reduction of oxygen content and to avoid detrimental effects on the organism and the oxidase and its substrate. The temperature for the method, will generally range from about 0° to 50° C., more usually from about 4° to 30° C.

It may be desirable to employ a substance to increase the viscosity of the medium containing the anaerobic microorganism in an amount sufficient to reduce the diffusion of oxygen into the medium. Such a substance can be, for example, an alginate, xanthum gum or the like. Usually, the viscosity increasing substance is present in the medium at a level of about 0.1 to 10% by weight, preferably about 0.5 to 3% by weight.

A particular application of a method in accordance with the present invention, by way of example and not limitation, is the transport of anaerobic microorganisms. Various disease states can be determined by the medical community on the basis of results from assays for the presence of a particular anaerobic microorganism in a sample suspected of containing the organism. The sample can be obtained from the patient suspected of having a particular disease state. The sample can be a cell specimen such as, for example, a sample obtained from abscess fluid or abscess material, a sample obtained from normally sterile body fluids such as biopsy specimens, joint fluid, pericardial fluid, peritoneal fluid, spinal fluid, trans-tracheal aspirate, and the like, or an exfoliative cell specimen comprising either normally sterile or normally non-sterile material. By the term "exfoliative" is meant that the specimen comprises isolated cells or clumps of cells obtained by scraping or washing the surface of tissue, which cells are removed individually or in scales or laminae. In this manner the exfoliative cell specimen can be distinguished from excised tissue that is obtained by biopsy. Generally, the exfoliatitive cell specimen is obtained from a locus of interest on a mammalian host. The specimen can be obtained, for example, by scraping or washing of tissue at the locus. Depending on the nature of the tissue involved or the location of the tissue as the case may be, one may collect an exfoliative body fluid, such as for example, cervical mucus, which has been in contact with and may be said to have washed the tissue at the locus. The exfoliative specimen can be obtained in accordance with the usual techniques of exfoliative cytology. In the detection of cervical carcinoma, for example, a scraping from the cervix is taken, normally referred to as a "cervical smear". A sputum sample would provide an exfoliative specimen from the lung. The exfoliative cell specimen of normally non-sterile material can be taken, for example, from the cervix, vagina, uterus, bronchus, prostate, gastrointestinal tract including oral pharynx, mouth, etc., and exfoliative cell specimens of normally sterile material can be taken, for example, from impressions of the surface of tumors or cysts, the cut surface of biopsy specimens, e.g. lymph nodes, and serous fluids.

After the specimen is obtained, it is placed in a transport medium so that the specimen may be taken to a laboratory where it is cultured.

In accordance with the teaching of the present invention the specimen would be obtained and transported to the laboratory in the presence of an effective amount of an oxidase and substrate for the oxidase. The specimen can be placed in a liquid, generally aqueous, medium or the specimen may be left on the means for securing the specimen. Usually, the specimen is secured with a swab or other such device conventional in the art. When the specimen is to be placed in a liquid medium, the means for securing the specimen generally will be contacted with the liquid medium until a sufficient quantity of the specimen becomes suspended in the liquid medium. The specimen is generally transported in a container, preferably a closed container. The liquid medium containing the specimen, or the specimen on the means for securing the specimen, is placed in the container and is put in fluid contact with the oxidase and its substrate. The oxidase and its substrate will usually be present in a liquid medium or can be stored in dry form and dissolved in a liquid aqueous medium and after addition of the specimen. The container with the cells and the oxidase and its substrate will usually be closed for transport to the laboratory or other similar location. During the transport the oxidase catalyzes the reaction of its substrate with the oxygen present in the closed container and reduces the oxygen content of the fluid medium in which the cells are present. The aqueous medium containing the oxidase and its substrate can further contain a hydrogen peroxide scavenger in accordance with the present invention.

In a particular example of an embodiment in accordance with the present invention the cell specimen is collected on a suitable collector, for example, a swab, and placed in a device comprised of a test tube made of a suitable material compatible with the reagents such as, e.g., glass, plastic, and the like. The test tube contains a thick walled cylinder composed of a porous absorbent material that fits snugly into the test tube and provides a cylindrical inner chamber. The cylinder is sufficiently absorbent and hydrophilic to hold a volume of the oxidase/substrate solution sufficient to absorb all the oxygen in the tube. Generally, the pore size of the pores of the cylinder will be from about $0.2\mu$ to $100\mu$, preferably from about $1\mu$ to $50\mu$. The porous cylinder may be made of any insoluble material that is hydrophilic or can be rendered hydrophilic by coating with a surfactant or other material. Suitable materials for the cylinder include porous nylon, polystyrene, cellulose, polyvinylchloride, cellulose nitrate, plastic, silica, ceramics, paper and the like.

The thick walled cylinder can be stored dry or coated with oxidase, combination of the oxidase and its substrate, buffers, and hydrogen peroxide scavenger according to conventional methods for coating materials on surfaces. These materials can be bound to the cylinder by either physical or chemical means. Thus, a solution can be absorbed into the pores of the cylinder prior to use in the present invention or the liquid can be removed by evaporation for purpose of storage and then wet with an aqueous solution prior to use. Alternatively, some of these materials may be covalently bound to the cylinder. It is preferable that the liquid absorptive capacity of the cylinder material be high. Usually, it will be able to absorb at least 25% of its volume of water, probably at least 40%, most probably at least 60%.

The above device includes a means for closing the tubes, for example, a cap, which can conveniently have a telescopic fit with the test tube. The closing means can be rigid or flexible. In one embodiment the device will contain a breakable ampoule which contains water, and may also contain one or more of a group consisting of the oxidase, substrate for the oxidase, buffers and a hydrogen peroxide scavenger. The ampoule and the device are designed such that the ampoule can be broken, for example, by telescopically contacting the cap with the test tube or by flexing the cap or the tube, whereby the liquid in the ampoule is released and is absorbed into the wall of the cylinder. Either before or after breaking ampoule, the collector containing the specimen is placed in the inside of the cylinder. After the test tube is closed with the cap as described above, the oxygen in the device will be depleted and the specimen can be transported to the laboratory without loss of viability of the cells that may be present in the specimen.

A device which may be used in accordance with the above is depicted in FIG. 1.

The device comprises container 10, for example a test tube, with thick-walled, porous cylinder 12 and inner chamber 14. Cap 16 contains frangible ampoule 18 that preferably can be held in place by a plug of liquid-permeable material such as cotton or glass wool (20). Oxidase (22) is present on the surface of the material comprising cylinder 12. Frangible ampoule 18 contains substrate for the oxidase in aqueous solution. Means for collecting a specimen, for example, swab 24, is placed in inner chamber 14 and cap 16 is telescopically secured onto container 10. During this securing, or by squeezing cap 16 when cap is flexible, ampoule 18 is broken and the aqueous solution of substrate is dispensed onto porous cylinder 12 whereupon the solution is absorbed by the porous material and oxidase can react with the substrate.

A composition is accordance with the present invention comprises viable cells, an oxidase and its substrate in an amount sufficient to increase the time of survival of the viable cells, and, when the cells and the oxidase are present in the same solution, a hydrogen peroxide scavenger in an amount sufficient to avoid substantial loss of cell viability due to hydrogen peroxide generated by the oxidase. Generally, the composition in accordance with the present invention is present in an aqueous medium or may be contained in two solutions that are in fluid contact in a closed container, one of which contains the cells and the other the oxidase and substrate.

To enhance the versatility of the subject method the reagents can be provided in packaged combination, in the same or separate containers, so that the ratio of the reagents provides for substantial optimization of the method and the assay. Thus, the present invention also includes a kit for securing a cell sample and preserving the sample. The kit comprises in packaged combination an oxidase and its substrate in an amount sufficient to increase the time the cells are viable during storage. The kit can further include means for securing a cell sample and additionally a container for the sample. The kit can further comprise a hydrogen peroxide scavenger in an amount sufficient to reduce the level of hydrogen peroxide generated by the oxidase.

EXAMPLES

The invention is further demonstrated by the following illustrative examples.

EXAMPLE 1

The composition of the invention was evaluated as a transport medium for anaerobic microorganisms. The reagent employed as the transport medium had the following composition:
  250 mM glucose
  150 mM phosphate (Na+) pH 7.2
  20 $\mu$g/ml glucose oxidase (4.4 units/ml)
  10 $\mu$g/ml stabilized catalase
  0.1% rabbit serum albumin (RSA) in $dH_2O$ The transport medium was divided into two containers (9.9 ml of transport medium each) and each container was inoculated in an anaerobic chamber with 0.1 ml of a *Bacteroides fragilis* (*B. fragilis*) suspension adjusted to a density equal to 0.5 MacFarland standard. Aliquots (2 ml) from each container were taken and placed in separate vials having a capacity of 3 ml. One set of vials was maintained under anaerobic conditions at room temperature (control) and the other set of vials was maintained aerobically at room temperature.

At T=0, 2, 4, 6, and 24 hr. from the time of inoculation a vial from each set was taken into anaerobic chamber, diluted with anaerobic dilution medium that contained phosphate buffered saline, gelatin, cysteine, resazurin and had a redox potential of −150 millivolts, plated in triplicate onto nutrient medium plates, and incubated under standard anaerobic conditions. Plate counts were then determined; the results are found in Table 1.

TABLE 1

| | B. Fragilis (cfu × $10^6$ ML) | | | | |
|---|---|---|---|---|---|
| Hours after inoculation | 0 | 2 | 4 | 6 | 24 |
| Aerobic storage | 7.4 | 4.3 | 4.3 | 6 | 5.4 |
| Control (anaerobic conditions) | 7.4 | 4.3 | 4.0 | 6.8 | 6 |

The above example demonstrates that a significant level of protection of anaerobic microorganisms can be achieved in accordance with the present invention. The transport medium comprising glucose oxidase and glucose yielded substantially the same level of viability of B. fragilis when the organism was combined with the transport medium of the invention and stored under aerobic conditions as the level of viability obtained with storage under anaerobic conditions.

The invention has been described in detail with particular reference to the above embodiments. It will be understood, however, that variation and modifications can be effected within the spirit and scope of the invention.

What is claimed is:

1. A method for reducing the oxygen content of a fluid medium in which cells are present for the purpose of increasing the period during which said cells remain viable, which comprises having in contact with said fluid medium an effective amount of an oxidase and substrate for said oxidase to thereby increase the period of viability of said cells.

2. The method of claim 1 wherein said cells are of an anaerobic microorganism.

3. The method of claim 1 wherein said cells are of an anaerobic bacterium.

4. The method of claim 1 wherein said cells and said oxidase and said substrate for said oxidase are present in closed container.

5. The method of claim 1 wherein said fluid medium is air.

6. The method of claim 1 wherein said oxidase and said substrate for said oxidase are present in an aqueous medium.

7. The method of claim 1 wherein said cells are present in an aqueous medium.

8. The method of claim 7 wherein said oxidase and said substrate for said oxidase are in a liquid medium distinct from said aqueous medium.

9. The method of claim 2 wherein said oxidase and said substrate for said oxidase are present in a microbiological transport medium.

10. The method of claim 1 wherein said oxidase is a sugar oxidase.

11. The method of claim 1 wherein said oxidase is glucose oxidase.

12. The method of claim 1 wherein said method further comprises having present with said oxidase and substrate for said oxidase a hydrogen peroxide scavenger in an effective amount.

13. The method of claim 1 wherein said scavenger catalyses the disproportionation of hydrogen peroxide to oxygen and water.

14. The method of claim 12 wherein said scavenger is catalase.

15. The method of claim 6 wherein said oxidase is present in an amount of from about 0.02 to 20 International Units/ml and said substrate is present in an amount of from about $10^{-3}$ to 1 molar.

16. A method for extending the viability of an anaerobic microorganism, which comprises having present with said microorganism an effective amount of an oxidase and substrate for said oxidase to thereby increase the period of viability of said microorganism.

17. The method of claim 16 wherein said oxidase and substrate for said oxidase are in an aqueous medium.

18. The method of claim 17 wherein said medium and said microorganism are in combination.

19. The method of claim 17 wherein said medium and said microorganism are not in combination.

20. The method of claim 16 wherein said oxidase is a sugar oxidase.

21. The method of claim 16 wherein said method further comprises having present with said oxidase and said substrate a hydrogen peroxide scavenger in an effective amount.

22. The method of claim 17 wherein said oxidase is present in an amount of from about 0.02 to 20 International Units/ml and said substrate is present in an amount of from about $10^{-3}$ to 1 molar.

23. A composition comprising viable cells, an oxidase and its substrate in an amount sufficient to extend the viability of said cells, and a hydrogen peroxide scavenger in an amount sufficient to reduce the level of hydrogen peroxide generated by said oxidase.

24. The composition of claim 23 wherein said cells are an anaerobic microorganism.

25. The composition of claim 24 wherein said anaerobic microorganisms are selected from the group of clinically isolated bacteria consisting of Treponema spp., Selenomonas spp., Clostridium spp., Bacteroides spp., Peptostreptococcus spp., Peptococcus spp., Propionibacterium spp., Eubacterium spp., Veillonella spp., Actinomyces spp., Fusobacterium spp., Butyrivibrio spp., Succinivibrio spp., Succinimonas spp., Ruminococcus spp., Coprococcus spp., Arachnia spp., Bifidobacterium spp., Lactobacillus spp., Lachnospira spp., Leptotrichia spp., and Acidaminococcus spp.

26. The composition of claim 23 wherein said hydrogen peroxide scavenger is catalase.

27. The composition of claim 23 wherein said oxidase is a sugar oxidase.

28. The composition of claim 23 wherein said oxidase is glucose oxidase.

29. The composition of claim 23 wherein said oxidase is present in an amount of from about 0.02 to 20 International Units/ml and said substrate for oxidase is present in an amount of from about $10^{-3}$ to 1 molar.

* * * * *